United States Patent
Blondel et al.

(10) Patent No.: US 10,758,885 B2
(45) Date of Patent: Sep. 1, 2020

(54) USE OF AN AMPHOLYTE COPOLYMER AS COLLOIDAL STABILIZER IN A PROCESS OF ENCAPSULATING FRAGRANCE

(71) Applicant: S.P.C.M. SA, Andrezieux Boutheon (FR)

(72) Inventors: Frédéric Blondel, Andrezieux Boutheon (FR); Emmanuel Aussant, Paris (FR); Sandra Guinebretiere, Franconville (FR); Ian Michael Harrison, Poissy (FR); Guillaume Jeanson, Andrezieux Boutheon (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 0 days.

(21) Appl. No.: 16/331,166

(22) PCT Filed: Sep. 18, 2017

(86) PCT No.: PCT/EP2017/073518
§ 371 (c)(1),
(2) Date: Mar. 7, 2019

(87) PCT Pub. No.: WO2018/050899
PCT Pub. Date: Mar. 22, 2018

(65) Prior Publication Data
US 2019/0255501 A1 Aug. 22, 2019

(30) Foreign Application Priority Data

Sep. 19, 2016 (EP) .................................. 16306196

(51) Int. Cl.
*A61L 9/04* (2006.01)
*C11D 3/50* (2006.01)
*A61K 8/00* (2006.01)
*B01J 13/14* (2006.01)
*C11B 9/00* (2006.01)
*A61Q 19/00* (2006.01)
*A61K 8/81* (2006.01)
*A61K 8/11* (2006.01)
*A61K 8/87* (2006.01)
*A61Q 13/00* (2006.01)
*A61Q 5/12* (2006.01)
*A61Q 5/02* (2006.01)

(52) U.S. Cl.
CPC ................. *B01J 13/14* (2013.01); *A61K 8/11* (2013.01); *A61K 8/8158* (2013.01); *A61K 8/87* (2013.01); *A61Q 13/00* (2013.01); *A61Q 19/00* (2013.01); *C11B 9/00* (2013.01); *A61K 2800/56* (2013.01); *A61K 2800/654* (2013.01); *A61Q 5/02* (2013.01); *A61Q 5/12* (2013.01)

(58) Field of Classification Search
CPC .......... B01J 13/14; A61Q 19/00; A61Q 13/00; A61Q 5/02; A61Q 5/12; C11B 9/00; A61K 8/87; A61K 2800/56; A61K 8/01; A61K 8/8155; A61K 2800/654
USPC ........................................................ 512/4, 1
See application file for complete search history.

(56) References Cited

U.S. PATENT DOCUMENTS

| 5,609,862 | A | * | 3/1997 | Chen | A61K 8/8158 424/70.11 |
|---|---|---|---|---|---|
| 2005/0112152 | A1 | | 5/2005 | Popplewell et al. | |
| 2011/0077188 | A1 | | 3/2011 | Ouali et al. | |
| 2012/0148644 | A1 | | 6/2012 | Popplewell et al. | |
| 2013/0095158 | A1 | * | 4/2013 | Denuell | B01J 13/14 424/401 |
| 2014/0017287 | A1 | * | 1/2014 | Lei | B01J 13/14 424/401 |

FOREIGN PATENT DOCUMENTS

| WO | 0162376 A1 | 8/2001 |
|---|---|---|
| WO | 2009/153695 A1 | 12/2009 |
| WO | 2011/123730 A1 | 10/2011 |
| WO | 2011/161229 A1 | 12/2011 |
| WO | 2016/071153 A1 | 5/2016 |

OTHER PUBLICATIONS

International Search Report and Written Opinion of the International Searching Authority for International Application No. PCT/EP2017/073518 dated Nov. 7, 2017.

* cited by examiner

*Primary Examiner* — Jessica Whiteley
(74) *Attorney, Agent, or Firm* — Heslin Rothenberg Farley & Mesiti P.C.

(57) ABSTRACT

The invention relates to the use of an ampholyte copolymer as a colloidal stabilizer in the preparation of core-shell microcapsules containing a fragrance,
wherein the ampholyte copolymer comprises:
2 to 99 mol % of cationic monomer having at least one quaternary ammonium group,
1 to 98 mol % of acrylic based monomer,
0 to 97 mol % of non-ionic monomer,
and wherein the ampholyte copolymer has more cationic charges than anionic charges, wherein the cationic charges of the ampholyte copolymer are exclusively due to the at least one quaternary ammonium group of the cationic monomer.

20 Claims, No Drawings

USE OF AN AMPHOLYTE COPOLYMER AS COLLOIDAL STABILIZER IN A PROCESS OF ENCAPSULATING FRAGRANCE

CROSS REFERENCE TO RELATED APPLICATIONS

This application is a national stage filing under section 371 of International Application No. PCT/EP2017/073518, filed on Sep. 18, 2017, and published on Mar. 22, 2018 as WO 2018/050899, which claims priority to European Application No. 16306196.3, filed on Sep. 19, 2016. The entire contents of WO 2018/050899 are hereby incorporated herein by reference.

FIELD OF THE INVENTION

The present invention relates to the use of ampholyte copolymer as colloidal stabilizer in the preparation of a polyurea or polyurethane shell microcapsule encapsulating perfumes.

BACKGROUND OF THE INVENTION

A microcapsule is a substantially spherical object, which consists of a core and a wall (shell) material surrounding the core, wherein the core may be a solid, liquid or a gaseous component. For many applications the wall (shell) is formed by a polymer material. Microcapsules usually have a volume average diameter from 1 to 1000 µm.

A multitude of shell materials is known for producing the wall (shell) of microcapsules. The shell can consist either of natural, semisynthetic or synthetic materials. Natural shell materials are, for example, gum arabic, agar agar, agarose, maltodextrins, alginic acid or its salts, e.g. sodium alginate or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic shell materials are inter alia chemically modified celluloses, in particular cellulose esters and cellulose ethers, e.g. cellulose acetate, ethyl cellulose, hydroxypropylcellulose, hydroxypropylmethylcellulose and carboxymethylcellulose, and also starch derivatives, in particular starch ethers and starch esters. Synthetic shell materials are, for example, polymers, such as polyacrylates, polyamides, polyvinyl alcohol, polyvinylpyrrolidone, polyurea, polyurethane or aminoplast.

Polyurea core-shell microcapsules are of interest for home care, personal care and household care applications. To assure their adoption in these applications, they must exhibit deposition and adhesion properties on the substrate, such as textile, skin, hair, leaf or other surfaces.

It is known that positively charged microcapsules exhibit enhanced deposition when applied to a situs, such as fabric. Indeed, coating materials that are applied to microcapsules in order to impart a positive charge are sometimes referred to as "deposition aids".

Several prior art documents disclose cationic microcapsules, in particular polyurea core-shell microcapsules.

WO 01/62376 relates to microcapsules, wherein the surface of these microcapsules has a positive charge. The positive charge is created either by selecting wall (shell)-forming materials that are positively charged, or by modifying the capsule wall (shell) by applying a surface coating of a cationic compound, e.g. quaternary ammonium compounds, cationic polymers or emulsifiers.

WO 2011/123730 describes a process for coating microcapsules with a cationic polymer, wherein a sufficient amount of a cationic polymer is added to negatively charged pre-formed microcapsules in order to obtain a surface-modified microcapsule bearing a positive zeta potential.

US 2012/0148644 relates to polyurethane or polyurea microcapsules, which may be modified with a polymer, which is selected from an amphoteric or a cationic polymer, such as polyquaternium-6, polyquaternium-47, polyvinylamine and its copolymers with vinylformamide.

U.S. Pat. No. 8,426,353 relates to perfume-containing polyurea microcapsules. The microcapsules are obtained from a mixture of polyisocyanates and a colloidal stabilizer which is an aqueous solution of a polyvinyl alcohol and of a cationic copolymer of vinylpyrrolidone and of a quaternized vinylimidazol. The polyisocyanates and the polyvinyl alcohol react together while the cationic copolymer can be easily removed. Indeed, the cationic copolymer is non-covalently bound to the capsule shell and thus is easily washed off from the capsule wall (shell) during the manufacture.

Despite the extensive literature devoted to the provision of encapsulated perfumery, there is currently no commercially acceptable encapsulated perfume composition that is easy to manufacture, stable and provides good deposition while delivering good olfactive performance.

SUMMARY OF THE INVENTION

The invention relates to using an ampholyte copolymer as colloidal stabilizer in a method for the preparation of core-shell microcapsules in which the core comprises a fragrance. This ampholyte copolymer improves:
  the stability of the emulsion in which the microcapsules are formed;
  the control of the thickness of the microcapsules' shell;
  the prevention of the formation of agglomerates of microparticles;
  the stability of an aqueous composition, or slurry, comprising the microcapsules.

DETAILED DESCRIPTION OF THE INVENTION

The invention is based on the surprising discovery that by using a positively charged species as a colloidal stabilizer during the preparation of microcapsules containing a fragrance, it is possible to incorporate a positive charge into the shell that remains substantially constant and is not washed out. Furthermore, this can be achieved without negatively affecting the physical stability of the capsule or its olfactive performance.

The use of an anionically modified isocyanate in the presence of a positively charged colloidal stabilizer facilitates the emulsion formation. Without wishing to be bound by any particular theory, applicant believes that the anionically modified isocyanate and the positively charged colloidal stabilizer form a stable complex due to the opposite charges.

Polymers, acting as protective colloids stabilizer, ensure that stable oil-in-water emulsions are formed; they ensure that pre-condensates and cross-linking agents are present at the oil-water interface in high concentration; and they provide a template around which the pre-condensates and cross-linking agents can react to form the encapsulating polymeric shells. Colloidal stabilizers are polymer systems which, in suspensions or dispersions, prevent a clumping together (agglomeration, coagulation, flocculation) of the emulsified, suspended or dispersed components. Within the context of the invention described herein, the colloidal stabilizer may also have emulsifying properties.

An ampholyte copolymer, in accordance with the present invention is defined herein below. It contains both cationic and anionic charges. Its cationic charges are pH independent. In other words, regardless of the solution in which the polymer may be solubilized or suspended, its cationic charge density remains the same.

Accordingly, the present invention relates to the use of an ampholyte copolymer as a colloidal stabilizer in the preparation of a core-shell microcapsules, containing a fragrance, which microcapsules are the reaction product of at least one anionically modified polyisocyanate with at least one polyamine or at least one polyfunctional alcohol, wherein the ampholyte copolymer comprises:
2 to 99 mol % of cationic monomer having at least one quaternary ammonium group, preferably one quaternary ammonium group;
1 to 98 mol % of acrylic based monomer;
0 to 97 mol % of non-ionic monomer;
and wherein the ampholyte copolymer has more cationic charges than anionic charges.

In another embodiment, the present invention relates to the use of an ampholyte copolymer as a colloidal stabilizer in the preparation of a core-shell microcapsules, containing a fragrance, which microcapsules are the reaction product of at least one anionically modified polyisocyanate and at least one nonionic polyisocyanate with at least one polyamine or at least one polyfunctional alcohol, wherein the ampholyte copolymer comprises:
2 to 99 mol % of cationic monomer having at least one quaternary ammonium group, preferably one quaternary ammonium group;
1 to 98 mol % of acrylic based monomer;
0 to 97 mol % of non-ionic monomer;
and wherein the ampholyte copolymer has more cationic charges than anionic charges.

The ratio of cationic and anionic functionalities is therefore greater than 1.

The cationic charges of the ampholyte copolymer are exclusively due to the quaternary ammonium group(s) of the cationic monomer.

The presence of a non-ionic monomer is optional.

Here and thereafter, the total mole percentage of monomers is 100. The skilled man in the art will be able to adjust the respective mole percentages of the cationic monomer, acrylic based monomer (anionic) and non-ionic monomer so as to reach 100.

According to a particular embodiment, the ampholyte copolymer may be used as colloidal stabilizer in a method for preparing core-shell microcapsules containing fragrance according to the following steps:
preparation of an aqueous phase comprising the ampholyte copolymer, at least one anionically modified polyisocyanate and at least one fragrance ingredient;
coacervation or emulsification of the resulting composition;
addition of at least one polyfunctional amine or at least one polyfunctional alcohol to initiate the polyaddition reaction.
forming a dispersion of microcapsules by heating the mixture;

According to a particular embodiment, the ampholyte copolymer may be used as colloidal stabilizer in a method for preparing core-shell microcapsules containing fragrance according to the following steps:
preparation of an aqueous phase comprising the ampholyte copolymer, at least one anionically modified polyisocyanate, at least one non-ionic polysiocyanate and at least one fragrance ingredient;
coacervation or emulsification of the resulting composition;
addition of at least one polyfunctional amine or at least one polyfunctional alcohol to initiate the polyaddition reaction.
forming a dispersion of microcapsules by heating the mixture;

The resulting microcapsules are preferably suspended in the aqueous phase. The resulting suspension may be used without any purification step, or eventually dried. The aqueous phase generally comprises at least some of the ampholyte copolymer.

According to another particular embodiment, once the core-shell microcapsules are formed, a cationic copolymer may be added to the resulting composition, so as to improve the stability of the aqueous composition, or slurry, comprising the microcapsules.

The core-shell microcapsules prepared by the process described above are typically collected in the form of a slurry comprising a plurality of microcapsules suspended in a suitable suspending medium.

As already mentioned, the ampholyte copolymer of the invention comprises at least one cationic monomer (2-99 mol %), at least one acrylic based monomer (1-98 mol %) and optionally at least one non-ionic monomer (0-97 mol %).

The cationic monomer(s) may be chosen, in particular, from monomers such as derivatives of the following monomers having a quaternary ammonium group: acrylamide, acrylic, vinyl, allyl or maleic. In particular, and in a non-limiting way, the cationic monomer is preferably selected from the group consisting of quaternized dimethylaminoethyl acrylate (ADAME), quaternized dimethylaminoethyl methacrylate (MADAME), dim ethyl diallyl ammonium chloride (DADMAC), acrylamidopropyltrimethylammonium chloride (APTAC) and methacrylamidopropyltrimethylammonium chloride (MAPTAC). The cationic monomer may also be a mixture of cationic monomers. The most preferred cationic monomer is MAPTAC.

The cationic monomer represents 2 to 99 mole %, preferably 30 to 95 mole %, more preferably 60 to 90 mole %, as compared to the total number of moles of monomers of the ampholyte copolymer.

The acrylic based monomers may be selected from monomers having acrylic, vinyl, maleic, fumaric or allyl functionalities and having a carboxy, phosphonate, sulfonate or other group with an anionic charge. It may also be the ammonium salt or alkaline-earth metal salt or alkaline metal salt of such monomers.

Examples of suitable acrylic based monomers include acrylic acid, methacrylic acid, itaconic acid, crotonic acid, maleic acid, fumaric acid and strong-acid monomers, for example monomers with a sulfonic or a phosphonic acid-type function such as 2-acrylamido-2-methylpropane sulfonic acid, vinylsulfonic acid, vinylphosphonic acid, allylsulfonic acid, allylphosphonic acid, styrene sulfonic acid. The acrylic based monomer may also be any water-soluble salts of these monomers; wherein the salt is a salt of an alkali metal, an alkaline-earth metal or an ammonium. It may also be a mixture of acrylic based monomers. The most preferred acrylic based monomer is acrylic acid, methacrylic acid, or a water soluble salt thereof.

The acrylic based monomer represents 1 to 98 mole %, preferably 5 to 70 mole %, more preferably 10 to 40 mole %, as compared to the total number of moles of monomers of the ampholyte copolymer.

Optionally, the ampholyte copolymer comprises at least one non-ionic monomer. The useful non-ionic monomer in this invention can be selected from the group including water-soluble vinyl monomers. The preferred non-ionic monomer belonging to this category is advantageously selected from the group consisting of acrylamide, methacrylamide, N-isopropylacrylamide, N,N-dimethylacrylamide, N-methylolacrylamide. N-vinylformamide, N-vinyl acetamide, N-vinylpyridine and/or N-vinylpyrrolidone can also be used. It may also be a mixture of non-ionic monomers. The most preferred non-ionic monomer is acrylamide.

The non-ionic monomer represents 0 to 97 mole %, preferably 0 to 80 mole %, more preferably 0 to 50 mole %, as compared to the total number of moles of monomers of the ampholyte copolymer.

The ampholyte copolymer contains cationic and acrylic based monomers and optionally non-ionic monomers. The ampholyte copolymer has a ratio of cationic and anionic functionalities resulting in a net total charge of positive. In other words, the ampholyte copolymer has a greater number of positive functions that generally result from the cationic monomer as compared to the number of negative functions that generally result from the acrylic based monomer. The molar percentage of cationic monomer is preferably greater than the molar percentage of acrylic based monomer.

According to a preferred embodiment, the ampholyte copolymer comprises:
   30 to 95 mol % of methacrylamidopropyltrimethylammonium chloride (MAPTAC), preferably 60 to 90 mol %;
   5 to 70 mol % of acrylic acid or a water soluble salt thereof, preferably 10 to 40 mol %;
   0 to 80 mol % of acrylamide, preferably 0 to 50 mol %.

Preferably, the ampholyte copolymer has a molecular weight of at least 100,000 g/mol, and more preferably of at least 500,000 g/mol.

The amount of polymeric stabilizer (ampholyte copolymer) that may be employed in a method for preparing a microcapsule according to the present invention may range from 0.001% to 20%, preferably 0.01 to 10%, more preferably 0.01 to 5% by weight based on the weight of the composition allowing the formation of the microparticles for instance the above mentioned aqueous phase.

The amount of polymeric stabilizer (ampholyte copolymer) that may be employed in a microcapsule composition (preferably a slurry) according to the present invention may range from 1% to 20%, more preferably 2 to 10% by weight based on the weight of the composition.

In general, the ampholyte copolymer of the invention does not require the development of any specific polymerization process. Indeed, it may be obtained according to all the polymerization techniques well known to a person skilled in the art. These known polymerization techniques include solution polymerization; gel polymerization; precipitation polymerization; inverse emulsion polymerization; aqueous emulsion polymerization; suspension polymerization; and micellar polymerization.

According to the invention, and in an advantageous manner, the ampholyte copolymer is not crosslinked. It may be linear or structured. A structured copolymer may be branched, star-shaped (in the form of a star) or comb-shaped (in the form of a comb). These structures may be obtained by free selection of the initiator, the transfer agents, the polymerization technique such as controlled radical polymerization, the incorporation of structural monomers, the concentration, etc. Suitable structural monomers include polyvalent metal salts, formaldehyde, glyoxal, or also, and preferably, covalent crosslinking agents capable of copolymerizing with the monomers and preferably monomers having polyethylenic unsaturation (having a minimum of two unsaturated functional groups), such as, for example, methylene bisacrylamide (MBA), triallyamine, polyethylene glycol diacrylate. Alternatively, macro initiators such as polyperoxides, polyazo compounds and polytransfer agents such as polymercaptan polymers may be used.

According to the invention, the ampholyte copolymer is present in aqueous continuous phase of the emulsion before the formation of the microcapsule. It is preferably also present in the aqueous phase before formation of the emulsion. It may be added during the formation of the emulsion.

According to the invention, the fragrance is present before the formation of the microcapsule.

According to the invention the fragrance includes scents that are floral, ambery, woody, leather, chypre, fougere, musk, mint, vanilla, fruit, and/or citrus. Fragrance oils are obtained by extraction of natural substances or synthetically produced. In one embodiment, the fragrance oil is one or more of an essential oil.

Without putting forward any theory, at the end of the formation of microcapsule, the ampholyte copolymer seems embedded in the shell, and unlike the prior art post-coating method, the copolymer cannot be washed out. As a result, the charge on the microcapsules is stable, or substantially stable, over time and insensitive, or substantially insensitive, to the conditions of the external suspending medium.

Although it was entirely surprising that a positively charged ampholyte copolymer could act as a colloidal stabilizer, it also considerably simplifies the manufacturing process. Furthermore, it enables a precise control of the microcapsule shell thickness, of the shell quality. It also enables to predict the release rates of fragrance.

In an embodiment of the invention, the shell of the core-shell microcapsule in the invention is made of a reaction product of a mixture of:
   at least two different polyisocyanates comprising at least one nonionic polyisocyanate (A) and at least one anionically modified polyisocyanate (B),
   and at least one polyfunctional amine.

In general, isocyanates are N-substituted organic derivatives (R—N=C=O) of isocyanic acid (HNCO) tautomeric in the free state with cyanic acid. Organic isocyanates are compounds in which the isocyanate group (—N=C=O) is bonded to an organic radical. Polyfunctional isocyanates are compounds with two or more (e.g. 3, 4, 5, etc.) isocyanate groups in the molecule.

Nonionic polyisocyanates can be selected from the group consisting of isocyanates useful in the formation of polyurea microcapsules include di- and tri-functionalised isocyanates such as 1,6-diisocyanatohexane, 1,5-diisocyanato-2-methylpentane, 1,5-diisocyanato-3-methylpentane, 1,4-diisocyanato-2,3-dimethylbutane, 2-ethyl-1,4-diisocyanatobutane, 1,5-diisocyanatopentane, 1,4-diisocyanatobutane, 1,3-diiocyanatopropane, 1,10-diisocyanatodecane, 1,2-diisocyanatocyclobutane, bis(4-isocyanatocyclohexyl)methane, or 3,3,5-trimethyl-5-isocyanatomethyl-1-isocyanatocyclohexane, isophorone diisocyanate (IPDI), hexamethylene 1,6 diisocyanate (HDI), hydrogenated 4,4 diphenyl methane diisocyanate (HMDI).

Anionically modified polyisocyanates preferably contain at least two isocyanate groups and at least one functional group, selected from anionic/aniogenic groups, polyethylene groups and combinations thereof. Suitable anionic or aniogenic groups are carboxylic acid groups, sulfonic acid groups, phosphonic acids groups and the salts thereof.

Suitable anionically modified polyisocyanates are described in US 2004/0034162 which is incorporated herein by reference.

For example, anionically modified polyisocyanates can be selected from anionically modified hexamethylene diisocyanate, isophorone diisocyanate, dicyclohexylmethane-4,4'-diisocyanate, the isocyanurate of hexamethylene diisocyanate or mixtures thereof.

In the sense of the invention, the term polyfunctional amine denotes amines that comprise at least two groups capable of reacting with NCO groups, wherein at least one of the groups capable of reacting with NCO groups is a primary or secondary amino group. When the polyfunctional amine contains only one primary or secondary amino group, it will contain one or more additional functional groups that are capable of reacting with NCO groups in a polymerisation reaction.

Reaction of NCO groups with amine groups leads to the formation of urea groups.

In a preferred embodiment, the polyfunctional amine comprises or consists of at least one polyethylenimine.

As an alternative to the amines discussed above, also compounds with hydroxyl groups, in particular preferably polyfunctional alcohols, can be used to react with NCO groups and thereby forming polyurethane. Suitable hydroxyl groups containing compounds can be selected from the group consisting of polycarbonate diols, sulfonated polyols, polyvinyl alcohols, cellulose derivatives, polyethylene glycol (PEG), polyester polyol, polycaprolactone polyol, resorcinol, polyacrylic acid, starch and triethanolamine.

Reaction of NCO groups with OH groups leads to the formation of urethane groups.

An important parameter of the microcapsules composition of the invention is volume average diameter. The microcapsules according to the invention have a volume average diameter of 2 to 90 μm, particularly 5 to 60 μm, and more particularly 10 to 30 μm. The volume average diameter may be obtained by conducting light scattering measurements, using techniques generally known in the art. For instance a Malvern 2000S instrument may be used.

The invention and its advantages will become more apparent to one skilled in the art from the following examples.

EXAMPLES

Preparation of an Amopholyte Polymer [AP] According to the Invention

The polymer of the invention is obtained using the following protocol. The example is carried out with an acrylic acid/MAPTAC copolymer. In order to produce this polymer, the following compounds are introduced in the reactor:

464 g of MAPTAC (50% in water)
34.4 g of Acrylic acid (90% in water)
119 g of water
0.03 g of EDTA
0.14 g of sodium hypophosphite The pH of the reaction medium is adjusted at 5.0-5.2, by using NaOH.

53 g of 2,2'-azobis (2-amidinopropane) di-hydrochloride (10% in water) are also introduced in the reactor.

The reaction medium is maintained at 85° C. during 1 hour. Then 1.3 g of sodium bisulfite solution (40% in water) is added in one shot in the reactor. After 1 hour of aging, the product is diluted by adding 255 g of water.

Example 1

An aqueous solution of 100 g polymer [AP] and 450 g water was prepared and the pH was adjusted to 9 using buffer salts. A mixture comprising 300 g perfume to be encapsulated, 20 g Desmodur® W1 (dicyclohexylmethane diisocyanate) and 8 g Bayhydur® XP 2547 (anionically modified isocyanurates of hexamethylene diisocyanate) was prepared. The aqueous solution and the mixture were combined and emulsified at room temperature by means of a stirring device. The emulsification process was carried out to the desired droplet size. Then 10 g of Lupasol® G100 solution (linear polyethyleneimine) was added in one step. The reaction mixture was heated gradually to 80° C. for 4 h. After the interfacial polymerization, 12 g of ammonia solution and 0.4 g Natrosol 250HX were added. The mixture was then cooled down to room temperature.

An encapsulated perfume composition was obtained. The volume average capsule size distribution, obtained with light scattering measurements using a Malvern 2000S instrument, was D50=10 μm and D 90=30 μm with a shell weight 6% of total slurry weight composition. The solid content of the slurry was 45 weight %.

Comparative Example 2: The process of Example 1 has been modified:

450 g water was provided and the pH was adjusted to 9 using buffer salts. A mixture comprising 300 g perfume to be encapsulated, 20 g Desmodur® W1 and 8 g Bayhydur® XP 2547 was prepared. The aqueous solution and the mixture were combined and stirred at room temperature by means of a stirring device. The stirring was carried out to the desired droplet size. Then 10 g of Lupasol® G100 solution was added in one step. The reaction mixture was heated gradually to 60° C. and an aqueous solution of 100 g [AP] was added. Then, the reaction mixture was further heated to 80° C. for 2 h. Thereafter, 12 g of ammonia solution and 0.4 g Natrosol 250HX were added. The mixture was then cooled down to room temperature.

The solid content of the obtained slurry was 12 weight %, which means that the fragrance composition was not well encapsulated, as it is far below the theoretical value of about 45%.

Example 2

TABLE 1

Influence of isocyanates and colloidal stabilizer on emulsion stability and olfactive performance of obtained capsules

| entry | % anionically modified isocyanate in oil phase | % nonionical isocyanate in oil phase | % positively charged colloidal stabilizer in aq. phase | olfactive performance in application | emulsion stability |
|---|---|---|---|---|---|
| 1 | 2 | 6 | 5 | +++ | +++ |
| 2 | 3 | 10 | 5 | +++ | +++ |
| 3 | 0 | 13 | 5 | ++ | ++ |
| 4 | 8 | 0 | 5 | ++ | +++ |

TABLE 1-continued

Influence of isocyanates and colloidal stabilizer on emulsion stability and olfactive performance of obtained capsules

| entry | % anionically modified isocyanate in oil phase | % nonionical isocyanate in oil phase | % positively charged colloidal stabilizer in aq. phase | olfactive performance in application | emulsion stability |
|---|---|---|---|---|---|
| 5 | 13 | 0 | 5 | ++ | +++ |
| 6 | 3 | 10 | — (5)* | + | +++ |

*Comparative example using neutral colloidal stabilizer polyvinyl pyrrolidone (PVP) instead of positively charged colloidal stabilizer To assess the olfative performance, the encapsulated perfume composition was tested in a rinse-off hair conditioner product on calibrated hair swatches (same quality, length, width & weight). All samples have the same maceration (3-4 days).

In a first step, the swatches are washed with un-fragranced shampoo, wherein the water temperature, the shampoo amount, the washing time and the rinsing time are defined. In a second step, a defined amount of conditioner comprising the encapsulated fragrance composition is dispensed on the hair swatch, it is massaged softly into the swatch for a defined time, leaved on swatch for a defined time and then rinsed off. The swatches are left to dry naturally at room temperature. The olfative performance is assessed at dry stage before and after combing.

The emulsion stability was rated on visual inspection and by comparing the particle size for a given rpm emulsion mill.

From Table 1 it can be seen that a stable emulsion can be obtained by reacting a mixture of isocyanates (comprising an anionically modified isocyanate and a non-ionic isocyanate, in different ratios) with polyamines in the presence of a positively charged colloidal stabilizer (Entry 1 and 2). The obtained capsules show good olfactive performance.

If a positively charged colloidal stabilizer is mixed with a non-ionic isocyanate, the obtained emulsion is less stable (Entry 3). In contrast to that, the mixture of a positively charged colloidal stabilizer with an anionically modified isocyanate gives a stable emulsion (Entry 4 and 5). However, the olfactive performance is better with 2 types of isocyanates, one anionically with one hydrophobic one. A mixture of an anionically modified isocyanate/a non-ionic isocyanate and a neutral colloidal stabiliser also gives a stable emulsion (Entry 6). However, the performance of the resulting capsules is less good if compared with Entry 1 and 2.

The invention claimed is:

1. A method for preparing core-shell microcapsules containing a fragrance, the method comprising, in the presence of an ampholyte copolymer used as a colloidal stabilizer, reacting at least one anionically modified polyisocyanate with at least one polyamine or at least one polyfunctional alcohol,
    wherein the ampholyte copolymer comprises:
    2 to 99 mol % of cationic monomer having at least one quaternary ammonium group,
    1 to 98 mol % of acrylic based monomer,
    0 to 97 mol % of non-ionic monomer,
    and wherein the ampholyte copolymer has more cationic charges than anionic charges, wherein the cationic charges of the ampholyte copolymer are exclusively due to the at least one quaternary ammonium group of the cationic monomer.

2. The method according to claim 1, wherein the microcapsules are made of the reaction product of at least one anionically modified polyisocyanate and at least one non-ionic polyisocyanate with at least one polyamine or at least one polyfunctional alcohol.

3. The method according to claim 1, wherein the cationic monomer is chosen from the group consisting of quaternized dimethylaminoethyl acrylate (ADAME), quaternized dimethylaminoethyl methacrylate (MADAME), dimethylfiallylammonium, chloride (DADMAC), acrylamindopropltrimethylammonium chloride (APTAC) and methacrylamidopropyltrimethylammonium chloride (MAPTAC).

4. The method according to claim 1, wherein the cationic monomer is methacrylamidopropyltrimethylammonium chloride (MAPTAC).

5. The method according to claim 1, wherein the acrylic based monomer is chosen from the group consisting of acrylic acid, methacrylic acid, itaconic acid, crotonic acid, maleic acid, fumaric acid, 2-acrylamido-2-methylpropane sulfonic acid, vinylsulfonic acid, vinylphosphonic acid, allylsulfonic acid, allylphosphonic acid, styrene sulfonic acid, and their water-soluble salts of an alkali metal, alkaline-earth metal or ammonium.

6. The method according to claim 1, wherein the acrylic based monomer is (meth)acrylic acid or a water soluble salt thereof.

7. The method according to claim 1, wherein the ampholyte copolymer comprises the non-ionic monomer and said non-ionic monomer is chosen from the group consisting of acrylamide, methacrylamide, N-isopropylacrylamide, N N-dimethylacrylamide, N-methylolacrylamide, N-vinylformamide, N-vinyl acetamide, N-vinylpyridine and N-vinylpyrroli done.

8. The method according to claim 1, wherein the non-ionic monomer is acrylamide.

9. The method according to claim 1, wherein the ampholyte copolymer comprises 30 to 95 mol % of cationic monomer.

10. The method according to claim 1, wherein the ampholyte copolymer comprises 60 to 90 mol % of cationic monomer.

11. The method according to claim 1, wherein the ampholyte copolymer comprises 5 to 70 mol % of acrylic based monomer.

12. The method copolymer according to claim 1, wherein the ampholyte copolymer comprises 10 to 40 mol % of acrylic based monomer.

13. The method according to claim 1, wherein the ampholyte copolymer comprises:
    30 to 95 mol % of methacrylamidopropyltrimethylammonium chloride (MAPTAC);
    5 to 70 mol % of acrylic acid or a water soluble salt thereof; and
    optionally, acrylamide.

14. The method according to claim 1, wherein the ampholyte copolymer has a molecular weight of at least 100,000 g/mol.

15. The method according to claim 1, wherein the ampholyte copolymer has a molecular weight of at least 500,000 g/mol.

16. The method according to claim 13, wherein the ampholyte copolymer comprises:

60 to 90 mol % of methacrylamidopropyltrimethylammonium chloride (MAPTAC);

10 to 40 mol % of acrylic acid or a water soluble salt thereof; and acrylamide.

17. The method according to claim 2, wherein the cationic monomer is chosen from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC) and methacrylamidopropyltrimethylammonium chloride (MAPTAC); and the acrylic based monomer is chosen from the group consisting of acrylic acid, methacrylic acid, itaconic acid, crotonic acid, maleic acid, fumaric acid, 2-acrylamido-2-methylpropane sulfonic acid, vinylsulfonic acid, vinylphosphonic acid, allylsulfonic acid, allylphosphonic acid, styrene sulfonic acid, and their water-soluble salts of an alkali metal, alkaline-earth metal or ammonium.

18. The method according to claim 17, wherein the ampholyte copolymer comprises the non-ionic monomer and said non-ionic monomer is chosen from the group consisting of acrylamide, methacrylamide, N-isopropylacrylamide, N N-dimethylacrylamide, N-methylolacrylamide, N-vinylformamide, N-vinyl acetamide, N-vinylpyridine and N-vinylpyrrolidone.

19. The method according to claim 17, wherein the ampholyte copolymer comprises:

30 to 95 mol % of cationic monomer; and 5 to 70 mol % of acrylic based monomer.

20. The method according to claim 19, wherein the cationic monomer is methacrylamidopropyltrimethylammonium chloride (MAPTAC), the acrylic based monomer is (meth)acrylic acid or a water soluble salt thereof, and the ampholyte copolymer additionally comprises acrylamide.

* * * * *

UNITED STATES PATENT AND TRADEMARK OFFICE
CERTIFICATE OF CORRECTION

PATENT NO. : 10,758,885 B2
APPLICATION NO. : 16/331166
DATED : September 1, 2020
INVENTOR(S) : Blondel et al.

Page 1 of 1

It is certified that error appears in the above-identified patent and that said Letters Patent is hereby corrected as shown below:

In the Claims

Column 10, Line 12-13: Claim 3, Delete "dimethylfiallylammonium," and insert
-- dimethyldiallylammonium --

Column 10, Lines 37-38: Claim 7, Delete "N-vinylpyrroli done" and insert -- N-vinylpyrrolidone --

Column 10, Line 39: Claim 8, Delete "claim 1" and insert -- claim 7 --

Signed and Sealed this
Thirteenth Day of October, 2020

Andrei Iancu
*Director of the United States Patent and Trademark Office*